United States Patent [19]

Annen et al.

[11] 4,176,126

[45] Nov. 27, 1979

[54] NOVEL CORTICOIDS

[75] Inventors: Klaus Annen; Henry Laurent; Helmut Hofmeister; Rudolf Wiechert; Hans Wendt; Joachim-Friedrich Kapp, all of Berlin, Fed. Rep. of Germany

[73] Assignee: Schering Aktiengesellschaft, Berlin and Bergkamen, Fed. Rep. of Germany

[21] Appl. No.: 839,486

[22] Filed: Oct. 4, 1977

[30] Foreign Application Priority Data

Oct. 4, 1976 [DE] Fed. Rep. of Germany ....... 2645104

[51] Int. Cl.$^2$ .............................................. C07J 71/00
[52] U.S. Cl. ...................... 260/397.45; 260/239.55 D
[58] Field of Search ................................... 260/397.45

[56] References Cited

U.S. PATENT DOCUMENTS

| | | | |
|---|---|---|---|
| 2,808,415 | 10/1957 | Sarett | 260/397.45 |
| 2,813,882 | 11/1957 | Sarett | 260/397.45 |
| 3,312,590 | 4/1967 | Elks et al. | 260/397.45 |
| 3,813,420 | 5/1974 | Douglas et al. | 260/397.45 |

*Primary Examiner*—Elbert L. Roberts
*Attorney, Agent, or Firm*—Millen & White

[57] ABSTRACT

Novel corticoids of formula I

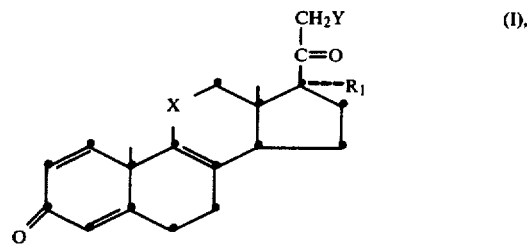

wherein X is β-hydroxymethylene, β-fluoromethylene or carbonyl; Y is fluorine, chlorine, hydroxy, or acyloxy of 1–10 carbon atoms; and R$_1$ is acyloxy of 1–10 carbon atoms, possess strong anti-inflammatory activity when administered topically and display only minor systemic side effects.

15 Claims, No Drawings

NOVEL CORTICOIDS

BACKGROUND OF INVENTION

This invention relates to novel corticoids, a process for the production thereof, and pharmaceutical preparation containing them as active agents.

The conventional, topically highly effective corticoids having low systemic side effects, for example betamethasone, diflucortolone, or fluocinonide are substituted in the 6- and/or 16-position of the steroid skeleton. The synthesis of these compounds is accordingly very expensive. This represents a significant disadvantage in view of the growing difficulty in finding sufficient quantities of starting materials for corticoid syntheses and in view of the otherwise high costs involved in using active agents for corticoid-containing drug specialties.

In contrast, corticoids unsubstituted in the 6- and 16-positions, can be synthesized much more readily. However, heretofore, despite intensive efforts, it has been impossible to find among these an active compound which shows an equivalent spectrum of effectiveness as compared to the aforementioned compounds.

SUMMARY OF THE INVENTION

It has now been found that heretofore unknown corticoids, unsubstituted in the 6- and 16-positions, show upon topical application surprisingly strong anti-inflammatory activity, which frequently surpasses that of the most active, commercially available corticoids; and that these corticoids cause only minor systemic side effects.

In a composition of matter aspect, this invention involves novel corticoids of the formula I

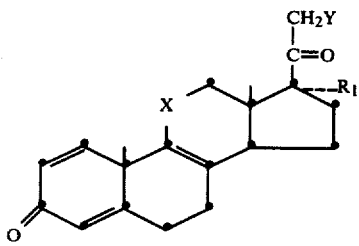

wherein X is $\beta$-hydroxymethylene, $\beta$-fluoromethylene, or carbonyl; Y is fluorine, chlorine, hydroxy, or acyloxy of 1–10 carbon atoms; and $R_1$ is acyloxy of 1–10 carbon atoms.

In another composition of matter aspect, this invention provides pharmaceutical compositions comprising an anti-inflammatorily effective amount of a compound of formula I and a pharmaceutically acceptable adjuvant.

In a method of use aspect, this invention provides a method of treating inflammation in mammals, includig humans, which comprises administering an anti-inflammatorily effective amount of a compound of formula I.

DETAILED DISCUSSION

Suitable acyloxy groups $R_1$ and Y include, for example, formyloxy, acetoxy, propionyloxy, butyryloxy, isobutyryloxy, valeryloxy, dimethylacetoxy, trimethylacetoxy, hexanoyloxy, ter.-butylacetoxy, heptanoyloxy, octanoyloxy, nonanoyloxy or decanoyloxy groups.

Suitable alkanoyloxy groups include $C_3$–$C_{10}$ cycloalkanoyloxy; phenyl- or benzoyloxy-substituted alkanoyloxy wherein the total carbon content is from 7 to 10 or $C_3$–$C_{10}$ carboxy-substituted alkanoyloxy; or phenyl-, carboxy- or benzoyloxy-substituted alkenoyloxy wherein the total carbon content is up to 10 carbon atoms. Acyloxy groups include for example cyclopropylpropionyloxy, cyclobutylcarbonyloxy, cyclopentylpropionyloxy, cinnamoyloxy, 2-phenylpropionyloxy, carboxyacetyloxy, $\omega$-carboxypropionyloxy, $\omega$-carboxybutyryloxy or $\omega$-carboxypentanoyloxy.

Especially preferred acyloxy groups $R_1$ and Y are the alkanoyloxy groups of 1–6 carbon atoms and the benzoyloxy group. The alkyl portions of the former may be straight chain or branched. Contemplated classes of compounds within the scope of formula I include those wherein:

(a) X is $\beta$-hydroxymethylene;
(b) X is $\beta$-fluoromethylene;
(c) X is carbonyl;
(d) Y is fluorine or chlorine including each of those of a–c;
(e) Y is hydroxy including each of those of a–c;
(f) Y is acyloxy of 1–10 carbon atoms including each of those of a–c; and
(g) R is acyloxy of 1–10 carbon atoms, including each of those of a–f.

The novel corticoids of this invention can be prepared according to several conventional processes. Such processes include, for example, those wherein:

(a) Hydrogen halide is split off from a corticoid of general Formula II

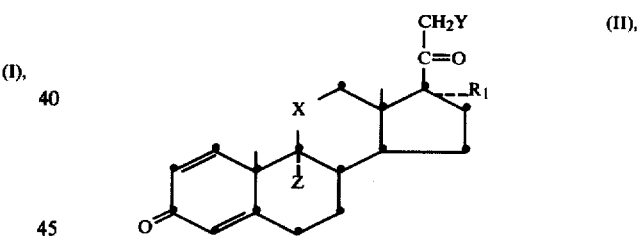

wherein
X,Y, and $R_1$ are as defined above and
Z is chlorine or bromine;
or (b) for the preparation of corticoids of formula I wherein Y represents a hydroxy group, an ortho ester of formula III

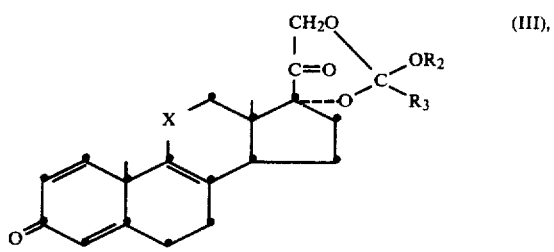

wherein
X is as defined above,
$R_2$ is alkyl of 1–4 carbon atoms, and $R_3$ is the hydrocarbon residue of the acyloxy group $R_1$, is split by hydrolysis;

or (c) for the preparation of corticoids of formula I wherein Y is fluorine, chlorine, or acyl, the 21-hydroxy group of a corticoid of formual Ia

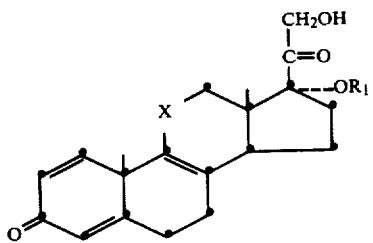

(Ia), wherein X and $R_1$ are as defined above, is appropriately esterified by the precursor of an acyloxy Y group, or exchanged for fluorine or chlorine, and optionally a β-hydroxymethylene group X present therein is oxidized to the carbonyl group.

The process of this invention according to variant (a) can be conducted under the conditions described in U.S. Pat. No. 3,845,085. To conduct process variant (b), the reaction conditions set forth in U.S. Pat. No. 3,152,154 and in DOS's [German Unexamined Laid-Open Aplications] Nos. 2,340,591 and 2,055,221 are suitable, for example. The exchange of the 21-hydroxy group for a fluorine or chlorine atom according to process variant (c) can be effected under the conditions disclosed in U.S. Pat. No. 3,721,686. The esterification of the 21-hydroxy group and the optionally following oxidation of the 11-hydroxy group likewise takes place according to conventional methods described, for example, in U.S. Pat. No. 3,828,083.

All starting materials required for these processes are also conventional. (J. Amer. Chem. Soc., 77, 1955, 4181)

As mentioned above, the corticoids of this invention possess upon topical application a strong anti-inflammatory activity but display only a very weak effect upon systemic application.

The local anti-inflammatory activity of the corticoids can be determined by means of the conventional vasoconstriction test.

On the backs of persons volunteering for the experiment, the stratum corneum was split up by the application and removal of an adhesive strip having a width of 2 cm. applied twenty times at the same spot, thus producing a pronounced hyperemia. Within the stripped area, 50 mg of an ointment preparation were applied to each one of a number of marked zones of a size of 4 cm². The ointment base without active ingredient served as the blank value. The color value of the untreated skin was set at 100 while that of the stripped skin was set at 0. The skin color value under vasoconstriction was correspondingly evaluated between 0 and 100.

In the following Table 1, average values were compiled as the result of examinations of various volunteers and various back areas. In these inventigations, the highly effective 6α, 9α-difluoro-11β-hydroxy-16α-methyl-21-valeryloxy-1, 4-pregnadiene-3,20-dione (difluocortolone 21-valerate) was utilized as the reference substance. The results in the table demonstrate that the compounds of this invention possess excellent anti-inflammatory activity even in extreme dilution.

TABLE 1

| | RESULTS OF THE VASOCONSTRICTION TEST | | | |
|---|---|---|---|---|
| | | Concentration | Vasoconstriction after | |
| No. | | in % | 4 Hours | 8 Hours |
| I | 6α,9α-Difluoro-11β-hydroxy-16α-methyl-21-valeryloxy-pregnadiene-3,20-dione | 0.00001 | 33% | 36% |
| II | 17α-Benzoyloxy-11β-hydroxy-21-trimethylacetoxy-1,4,8(9)-pregnatriene-3,20-dione | 0.00001 | 30% | 33% |
| III | 17α-Acetoxy-21-chloro-11β-hydroxy-1,4,8(9)-pregnatriene-3,20-dione | 0.00001 | 42% | 42% |
| IV | 21-Chloro-11β-hydroxy-17α-propionyloxy-1,4,8(9)-pregnatriene-3,20-dione | 0.00001 | 47% | 45% |
| V | 17α-Benzoyloxy-21-chloro-11β-hydroxy-1,4,8(9)-pregnatriene-3,20-dione | 0.00001 | 52% | 64% |

The systemic activity of the compounds of this invention was determined as follows with the aid of the well-known thymolysis test:

SPF [specific-pathogen free] rats weighing 70–110 g were adrenalectomized under ether narcosis. Six animals, respectively, formed each test group and received orally over a period of three days a defined amount of the test compound. On the fourth day, the animals were sacrificed and the weight of their thymus determined. The control animals were treated in the same way, but received a benzyl benzoate-castor -castor oil mixture without the test compound. From the thus-measured thymus weights, the amount of test compound at which a 50% thymolysis was observed was conventionally determined.

Furthermore, the systemic activity was determined with the aid of the adjuvant-edema test as follows:

SPF rats weighing 130–150 g were injected in the right hind paw with 0.1 ml of a 0.5% Mycobacterium butyricum suspension (obtainable from the U.S. company, Difco), in order to induce a center of inflammation. Prior to injection, the paw volume of the rats was measured. Twenty four hours after injection, the paw volume was measured once again to determine the extent of the edema. Thereafter, varying amounts of the test compound, was administered orally to the rats. After another 24 hours, the paw volume was again determined.

The control animals were treated in the same way but without any test compound.

From the thus-obtained paw volumes, the amount of test compound which was required to achieve a 50% reduction the paw edema was conventionally determined. Difluocotolone 21-valerate was also utilized in these tests as the comparison compound.

The results obtained in these tests are set forth in Table 2 below. The results demonstrate that the compounds of the present invention show only systemic side effects.

The novel compounds of this invention are suitable for use in pharmaceuticals in combination with the excipients customary in galenic pharmacy for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar skin disorders.

The specialty drugs are conventionally prepared by formulating the active agents together with suitable additives into the desired form for administration, such as, for example; solutions, lotions, ointments, creams, or plasters. In the thus-formulated medicinal agents, the effective agent concentration is dependent on the compound used and the form of application and can be easily determined by clinical tests under conventional considerations. In case of lotions and ointments, the preferred active agent concentration is from 0.001% to 1%.

The novel agents are also advantageously suitable for the preparation of inhalants, optionally in combination with the conventional excipients and auxiliary agents. These inhalants can be utilized for the therapy of allergic diseases of the respiratory tract, e.g. bronchial asthma or rhinitis.

limitative of the remainder of the disclosure in any way whatsoever.

The temperatures in the examples are set forth in degrees Celsius.

EXAMPLE 1

(a) 500 mg. of pyridine tosylate, evaporated twice under vacuum to dryness with benzene, is combined in 500 ml. of benzene and 200 ml. of dioxane with 5 g. of 9α-chloroprednisolone. At a bath temperature of 130°, 50 ml. of solvent is removed by distillation and 6 ml. of the triethyl ester of orthoformic acid is added thereto. Within 2.5 hours, the remainder of the benzene is distilled off and, after adding 2.4 ml. of pyridine, the mixture is concentrated under vacuum, thus isolating 17α,21-(1-ethoxyethylidenedioxy)-9α-chloro-11β-hydroxy-1,4-pregnadiene-3,20-dione as a yellow, oily mixture of epimers.

(b) A solution of the thus-obtained oil in 150 ml. of methanol is refluxed with a mixture of 54 ml. of 0.1N acetic acid and 6 ml. of 0.1-molar aqueous sodium acetate solution at 90°. The mixture is concentrated to dryness, added to water, and extracted with methylene chloride. The organic extracts are washed with water, dried, and evaporated under vacuum, thus obtaining 9.5 g. of crude 17α-acetoxy-9α-chloro-11β,21-dihydroxy-1,4-pregnadiene-3,20-dione.

(c) 5 g. of the above crude product in 100 ml. of pyridine is combined dropwise at 0° with 10 ml. of methanesulfonic acid chloride and agitated for another hour. After precipitation into ice water and extraction with methylene chloride, the organic phase is washed with water, dried over $Na_2SO_4$, and concentrated under vacuum. Crude yield: 5.89 g. of product which is chro-

TABLE 2

| | Results of the Thymolysis Test and the Adjuvant-Edema Test | | |
|---|---|---|---|
| No. | Compound | Thymolysis $ED_{50}$ in mg./kg. | Adjuvant Edema Test $ED_{50}$ in mg./kg. |
| I | 6α,9α-Difluoro-11β-hydroxy-16α-methyl-21-valeryloxy-1,4-pregnadiene-3,20-dione | 0.03 | 0.3 |
| II | 17α-Benzoyloxy-11β-hydroxy-21-trimethylacetoxy-1,4,8(9)-pregnatriene-3,20-dione | 5.5 | 10 |
| III | 17α-Acetoxy-21-chloro-11β-hydroxy-1,4,8(9)-pregnatriene-3,20-dione | 3.6 | 3.6 |
| IV | 21-Chloro-11β-hydroxy-17α-propionyloxy-1,4,8(9)-pregnatriene-3,20-dione | 2.0 | 2.0 |
| V | 17α-Benzoyloxy-21-chloro-11β-hydroxy-1,4,8(9)-pregnatriene-3,20-dione | 1.0 | 1.0 |

Such usage may also be carried out by fully conventional techniques including methods of formulation, determination of dosages and frequency of application, etc. e.g., for mammals including humans. (Brit. Med. J. 1958, 762 and U.S. Pat. No. 3,634,582).

The compounds of the general formula I are superior over the prior art analogs, since they are much easier to prepare than the equal or less effective prior art compounds and since they display lower systemic activity than the known compounds.

Without further elaboration, it is believed that one skilled in the art can, using the preceding description, utilize the present invention to its fullest extent. The following preferred specific embodiments are, therefore, to be construed as merely illustrative, and not matographed on 580 g. of silica gel with a methylene chloride acetone gradient (0–10% acetone), thus obtaining 2.8 g. of 17α-acetoxy-9α-chloro-11β-hydroxy-21-mesyloxy-1,4-pregnadiene-3,20-dione, m.p. 213°.

(d) 2 g. of 17α-acetoxy-9α-chloro-11β-hydroxy-21-mesyloxy-1,4-pregnadiene-3,20-dione in 80 ml. of hexamethylphosphoric triamide is stirred with 12 g. of lithium chloride for 4.5 hours at a bath temperature of 85°. After precipitation into ice water/sodium chloride, the mixture is filtered off. The residue is washed with water, taken up in methylene chloride, and washed once again. Drying over sodium sulfate and concentration under vacuum yields 1.5 g. of a crude product which is chromatographed on 150 g. of silica gel with a hexane-ethyl acetate gradient (0–50% ethyl acetate).

Yield: 400 mg. of 17α-acetoxy-21-chloro-11β-hydroxy-1,4,8-pregnatriene-3,20-dione, m.p. 207°.

EXAMPLE 2

(a) 5 g. of crude 9α-chloro-11β,21-dihydroxy-17α-propionyloxy-1,4-pregnadiene-3,20-dione prepared analogously to Example 1 in 50 ml. of pyridine is agitated overnight at room temperature with 6 g. of tosyl chloride. After precipitation into ice water, the mixture is extracted with methylene chloride, the extracts are washed with water and, after drying over sodium sulfate, concentrated under vacuum. Yield: 6.4 g. of a crude product which is purified on 640 g. of silica gel with a methylene chloride-acetone gradient (0–15% acetone). Yield: 4.2 g. of 9α-chloro-11β-hydroxy-17α-propionyloxy-21-tosyloxy-1,4-pregnadiene-3,20-dione, m.p. 165°-167°.

(b) 2 g. of 9α-chloro-11α-hydroxy-17α-propionyloxy-21-tosyloxy-1,4-pregnadiene-3,20-dione in 40 ml. of hexamethylphosphoric triamide is agitated with 8 g. of lithium chloride for 6 hours at a bath temperature of 85°. After precipitation into ice water, the mixture is filtered off; the residue is washed with water and taken up in methylene chloride. The organic solution is dried over sodium sulfate and concentrated under vacuum, yielding 1.4 g. of a crude product which is purified on 140 g. of silica gel with a hexane-ethyl acetate gradient (0-50% ethyl acetate). Yield: 500 mg. of 21-chloro-11α-hydroxy-17α-propionyloxy-1,4,8-pregnatriene-3,20-dione.

EXAMPLE 3

(a) 10 g. of 11β,17α,21-trihydroxy-1,4,8-pregnatriene-3,20-dione in 100 ml. of pyridine is stirred with 50 ml. of butyric anhydride for 2 hours at room temperature. The mixture is poured on ice water, filtered off, and the washed residue is taken up in methylene chloride. After washing and drying of the organic solution, the mixture is evaporated under vacuum, thus obtaining 12.1 g. of a crude product which is recrystallized from acetone/hexane, yielding 8.9 g. of 21-butyryloxy-11β,17α-dihydroxy-1,4,8-pregnatriene-3,20-dione.

(b) At 0° and under an argon atmosphere, 12.5 ml. of a 5% solution of methyllithium in ether is added dropwise to a suspension of 3 g. of copper(I) iodide in 60 ml. of dry tetrahydrofuran. The yellow mixture is cooled to −30° and then a solution of 2.8 g. of 21-butyryloxy-11β,17α-dihydroxy-1,4,8-pregnatriene-3,20-dione in 50 ml. of dry tetrahydrofuran is added. The mixture is stirred for 3 to 4 hours at this temperature, and the excess reagent is destroyed with an aqueous ammonium chloride solution. After extraction with methylene chloride, the organic solution is washed, dried over Na$_2$SO$_4$, and evaporated under vacuum, yielding 2.5 g. of crude 17α-butyryloxy-11β,21-dihydroxy-1,4,8-pregnatriene-3,20-dione.

(c) 2.5 g. of crude 17α-butyryloxy-11β,21-dihydroxy-1,4,8(9)-pregnatriene-3,20-dione in 25 ml. of pyridine is stirred with 3 g. of tosyl chloride overnight at room temperature. After precipitation into ice water, the mixture is extracted with methylene chloride. The extracts are washed with water and, after drying over sodium sulfate, concentrated under vacuum. Yield: 2.3 g. of a crude product which is purified on 250 g. of silica gel with a methylene chloride-acetone gradient (0–15% acetone), thus obtaining 1.5 g of 17α-butyryloxy-11α-hydroxy-21-tosyloxy-1,4,8,(9)-pregnatriene-3,20-dione.

(d) 1.5 g. of 17α-butyryloxy-11β-hydroxy-21-tosyloxy-1,4,8-pregnatriene-3,20-dione in 30 ml. of hexamethylphosphoric triamide is stirred with 5 g. of lithium chloride for 4 hours at a bath temperature of 70°. The mixture is then introduced into ice water and filtered off. The washed residue is taken up in methylene chloride. The organic solution is washed with water, dried over sodium sulfate, and concentrated under vacuum, resulting in 1.3 g. of a crude product which is purified on 140 g. of silica gel with a hexane-ethyl acetate gradient (0–50% ethyl acetate). Yield: 720 mg. of 17α-butyryloxy-21-chloro-11β-hydroxy-1,4,8-pregnatriene-3,20-dione.

EXAMPLE 4

(a) 10 g. of 11β,17α,21-trihydroxy-1,48-pregnatriene-3,20-dione is reacted analogously to Example 3(a) with n-valeric anhydride to yield 11β,17α-dihydroxy-21-valeryloxy-1,4,8-pregnatriene-3,20-dione, resulting in 11.5 g. of a crude product which is recrystallized from acetone/hexane; final yield: 8.2 g.

(b) Analogously to Example 3(b), 5 g. of 11β,17α-dihydroxy-21-valeryloxy-1,4,8-pregnatriene-3,20-dione is reacted with lithium dimethyl cuprate to obtain 3.5 g. of crude 11β,21-dihydroxy-17α-valeryloxy-1,4,8-pregnatriene-3,20-dione.

(c) 3.5 g. of the above crude product is reacted analogously to Example 3(c) to 11β-hydroxy-17α-valeryloxy-21-tosyloxy-1,4,8-pregnatriene-3,20-dione, yielding 3.2 g. of a crude product which is chromatographed on 360 g. of silica gel with a methylene chloride-acetone gradient (0–15% acetone), thus obtaining 1.9 g. of 11β-hydroxy-21-tosyloxy-17α-valeryloxy-1,4,8-pregnatriene-3,20-dione.

(d) 1.9 g. of the above tosylate is converted analogously to Example 3(d) with lithium chloride into the corresponding 2-chloro compound, yielding 1.8 g. of a crude product which is purified on 200 g. of silica gel with a hexane-ethyl acetate gradient (0–50% ethyl acetate). Final yield: 1.1 g. of 21-chloro-11β-hydroxy-17α-valeryloxy-1,4,8-pregnatriene-3,20-dione.

EXAMPLE 5

(a) Analogously to Example 3(a), 12 g. of 11β,17α,21-trihydroxy-1,4,8-pregnatriene-3,20-dione is reacted with caproic anhydride, thus isolating 14.1 g. of 21-hexanoyloxy-11β,17α-dihydroxy-1,4,8-pregnatriene-3,20-dione which is recrystallized from acetone/hexane, yielding 11 g. of final product.

(b) 8 g. of 21-hexanoyloxy-11β,17α-dihydroxy-1,4,8-pregnatriene-3,20-dione is converted analogously to Example 3(b) with lithium dimethyl cuprate into 17α-hexanoyloxy-11β,21-dihydroxy-1,4,8-pregnatriene-3,20-dione. Yield: 6.5 g. of crude product.

(c) Analogously to Example 3(c), 6.5 g. of the above crude product is reacted to obtain 17α-hexanoyloxy-11β-hydroxy-21-tosyloxy-1,4,8-pregnatriene-3,20-dione, resulting in 5.9 g. of a crude product which is chromatographed on 600 g. of silica gel with a methylene chloride-acetone gradient (0–15% acetone). Yield: 3.9 g. of 17α-hexanolyloxy-11β-hydroxy-21-tosyloxy-1,4,8-pregnatriene-3,20-dione.

(d) Analogously to Example 3(d), 3.9 g. of the above tosylate is reacted with lithium chloride, thus obtaining 3.2 g. of a crude product which is purified on 250 g. of silica gel with a hexane-ethyl acetate gradient (0–50% ethyl acetate). Yield: 2.3 g. of 21-chloro-17α-hexanoyloxy-11β-hydroxy-1,4,8-pregnatriene-3,20-dione.

EXAMPLE 6

(a) 12.9 g. of 11β,17α,21-trihydroxy-1,4,8-pregnatriene-3,20-dione in 240 ml. of pyridine is stirred with 18.5 g. of cyclohexanecarboxylic acid and 12.3 g. of N,N'-dicyclohexylcarbodiimide for 20 hours at room temperature. After precipitation into ice water, the mixture is worked up as usual and purified on 1.8 kg. of silica gel with a methylene chloride-acetone gradient (0–10% acetone), thus obtaining 8.2 g. of 21-cyclohexylcarbonyloxy-11β,17α-dihydroxy-1,4,8-pregnatriene-3,20-dione.

(b) 7 g. of 21-cyclohexylcarbonyloxy-11β,17α-dihydroxy-1,4,8-pregnatriene-3,20-dione is converted analogously to Example 3(b) with lithium dimethyl cuprate into 17α-cyclohexylcarbonyloxy-11β,21-dihydroxy-1,4,8-pregnatriene-3,20-dione, yielding 5.5 g. of a crude product.

(c) 5.5 g. of the above crude product is reacted analogously to Example 3(c) to 17α-cyclohexylcarbonyloxy-11β-hydroxy-21-tosyloxy-1,4,8-pregnatriene-3,20-dione, yielding 4.8 g. of a crude product which is chromatographed on 500 g. of silica gel with a methylene chloride-acetone gradient (0–15% acetone), thus obtaining 2.8 g. of 17α-cyclohexylcarbonyloxy-11β-hydroxy-21-tosyloxy-1,4,8-pregnatriene-3,20-dione.

(d) 2.8 g. of the above tosylate is reacted analogously to Example 3(d) with lithium chloride, yielding 2.3 g. of a crude product which is purified on 250 g. of silica gel with a hexane-ethyl acetate gradient (0–50% ethyl acetate). Final product: 1.2 g. of 21-chloro-17α-cyclohexylcarbonyloxy-11β-hydroxy-1,4,8-pregnatriene-3,20-dione.

EXAMPLE 7

(a) The procedure of Examples 1(a) and 1(b) is followed to produce 17α-butyryloxy-9α-chloro-11β,21-dihydroxy-1,4-pregnadiene-3,20-dione with the use of the triethyl ester of orthobenzoic acid.

(b) 7 g. of crude 17α-benzoyloxy-9α-chloro-11β,21-dihydroxy-1,4-pregnadiene-3,20-dione in 70 ml. of pyridine is reacted with 8 g. of tosyl chloride analogously to Example 2(a). Yield of crude product: 8.9 g. Purification on 900 g. of silica gel with a methylene chloride-acetone gradient (0–15% acetone) yields 5.1 g. of 17α-benzoyloxy-9α-chloro-11β-hydroxy-21-tosyloxy-1,4-pregnadiene-3,20-dione.

(c) 4 g. of the above tosylate is reacted analogously to Example 2(b) with lithium chloride, yielding 3.1 g. of crude product with is chromatographed on 350 g. of silica gel with a hexane-ethyl acetate gradient (0–50% ethyl acetate), thus obtaining 2.4 g. of 17α-benzoyloxy-21-chloro-11β-hydroxy-1,4,8-pregnatriene-3,20-dione, m.p. 196° (decomposition).

EXAMPLE 8

A mixture of 6.11 ml. of pyridine and 67.5 ml. of methylene chloride, cooled to 0°, is combined with incremental portions of 3.34 g. of chromium trioxide. The mixture is stirred for 15 minutes at room temperature and again cooled to 0°. 2.6 g. of crude 17α-benzoyloxy-21-chloro-11β-hydroxy-1,4,8-pregnatriene-3,20-dione in 56 ml. of methylene chloride is added dropwise to this solution, and the latter is agitated for 3.5 hours at room temperature. The mixture is then filtered off, the residue is treated repeatedly with methylene chloride, and the combined organic phases are washed with water. After drying over sodium sulfate, the mixture is evaporated under vacuum, yielding 3.9 g. of a crude product. After chromatography on 300 g. of silica gel with a methylene chloride-acetone gradient (0–10% acetone), 1.13 g. of 17α-benzoyloxy-21-chloro-1,4,8-pregnatriene-3,11,20-trione is obtained, m.p. 213°.

EXAMPLE 9

Analoguously to Example 8, 1.4 g. of 21-chloro-11β-hydroxy-17α-propionyloxy-1,4,8-pregnatriene-3,20-dione is oxidized. After the mixture has been worked up as usual and chromatographed, 1.26 g. of 21-chloro-17α-propionyloxy-1,4,8-pregnatriene-3,11,20-trione is isolated.

EXAMPLE 10

1.1 g. of 17α-butyryloxy-21-chloro-11β-hydroxy-1,4,8-pregnatriene-3,20-dione is oxidized analogously to Example 8, thus obtaining 8.5 g. of 17α-butyryloxy-21-chloro-1,4,8-pregnatriene 3,11,20-trione.

EXAMPLE 11

(a) 2.5 g. of 17α-benzoyloxy-9α-chloro-11β,21-dihydroxy-1,4-pregnadiene-3,20-dione in 50 ml. of HMPA is agitated with 2.5 g. of lithium chloride at 80° bath temperature for 3 hours. After the mixture has been worked up as usual, 2.2 g. of 17α-benzoyloxy-11βdihydroxy-1,4,8-pregnatriene-3,20-dione is isolated as a crude product.

(b) 2.2 g. of the above crude product in 44 ml. of pyridine is combined at 0° in incremental portions with 4.4 ml. of methaneusulfonic acid chloride and stirred for 10 minutes at this temperature. The mixture is then precipitated into ice water and worked up as usual, thus obtaining 2.2 g. of a crude product which is purified on 250 g. of silica gel with a methylene chloride-acetone gradient (0-15% acetone). Yield: 1.3 g. of 17α-benzoyloxy-11β-hydroxy-21-mesyloxy-1,4,8-pregnatriene-3,20-dione in the shape of a foam.

(c) 1.2 g. of the above mesylate in 40 ml. of dimethylformamide is agitated with 3.8 g. of potassium hydrogen fluoride for 72 hours under nitrogen at a bath temperature of 110°. The mixture is then precipitated into ice water and worked up as usual, yielding 1.8 g. of an oil which is purified on 135 g. of silica gel with a methylene chloride-acetone gradient (0–8% acetone). Yield: 214 mg. of 17α-benzoyloxy-21-fluoro-11β-hydroxy-1,4,8-pregnatriene-3,20-dione.

EXAMPLE 12

(a) 15 g. of 11β,17α,21-trihydroxy-1,4,8-pregnatriene-3,20-dione in 75 ml. of pyridine is reacted with 40 ml. of propionic anhydride analogously to Example 3(a), thus obtaining 16.2 g. of a crude product. Yield from acetone/hexane: 13.4 g. of 11β,17α-dihydroxy-21-propionyloxy-1,4,8-pregnatriene-3,20-dione.

(b) Analogously to Example 3(b), 12 g. of 11β,17α-dihydroxy-21-propionyloxy-1,4,8-pregnatriene-3,20-dione is rearranged with lithium cuprate to obtain the corresponding 17α-acyloxy compound. Crude yield: 10.8 g. of 11β,21-dihydroxy-17α-propionyloxy-1,4,8-pregnatriene-3,20-dione.

(c) 10 g. of crude 1β,21-dihydroxy-17α-propionyloxy-1,4,8-pregnatriene-3,20-dione is reacted analogously to Example 3(c) to 11β-hydroxy-17α-propionyloxy-21-tosyloxy-1,4,8-pregnatriene-3,20-dione. Yield: 7.2 g.

(d) 7 g. of the above tosylate in dimethylformamide is reacted analogously to Example 11 with potassium fluoride and purified. Yield: 1.2 g. of 21-fluoro-11β-hydroxy-17α-propionyloxy-1,4,8-pregnatriene-3,20-dione, m.p. 238°.

EXAMPLE 13

700 mg. of 21-fluoro-11β-hydroxy-17α-propionyloxy-1,4,8-pregnatriene-3,20-dione is oxidized analogously to Example 8. Yield: 530 mg. of 21-fluoro-17α-propionyloxy-1,4,8-pregnatriene:3,11,20-trione.

EXAMPLE 14

(a) Analgously to Example 1, 6 g. of 9α-chloro-11β-fluoro-17α,21-dihydroxy-1,4-pregnadiene-3,20-dione is reacted with the triethyl ester of orthobenzoic acid to obtain 11.1 g. of 17α-benzoyloxy-9α-chloro-11β-fluoro-21-hydroxy-1,4-pregnadiene-3,20-dione.

(b) A solution of 13 ml. of thionyl chloride in 10 ml. of hexamethylphosphoric triamide is agitated for 30 minutes at 0°. The solution is then combined with 8 g. of 17α-benzoyloxy-9α-chloro-11β-fluoro-21-hydroxy-1,4-pregnadiene-3,20-dione and agitated for another 5.5 hours at 0°. After precipitation into ice water and working the mixture up as usual, 9.6 g. of a crude product is isolated which is purified on 900 g. of silica gel with a methylene chloride-acetone gradient (0–15% acetone). Yield: 4.5 g. of 17α-benzoyloxy-9α,21-dichloro-11α-fluoro-1,4-pregnadiene-3,20-dione.

(c) A solution of 3.5 g. of 17α-benzoyloxy-9α,21-dichloro-11β-fluoro-1,4-pregnadiene-3,20-dione in 70 ml. of hexamethylphosphoric triamide is agitated with 3.5 g. of lithium chloride at a bath temperature of 40–50° for 17 hours. After precipitation in ice water and working up the mixture is usual, 7.5 g. of a crude product is isolated which is purified on 1.2 kg. of silica gel with a hexane-ethyl acetate gradient (4–40% ethyl acetate). Yield: 1.5 g. of 17α-benzoyloxy-21-chloro-11β-fluoro-1,4,8-pregnatriene-3,20-dione, m.p. 163° (decomposition).

EXAMPLE 15

(a) 10 g. of 11β,17α,21-trihydroxy-1,4,8-pregnatriene-3,20-dione is reacted analogously to Example 1 with the triethyl ester of orthoacetic acid. Subsequent hydrolysis yields 18.5 g. of 17α-acetoxy-11β,21 -dihydroxy-1,4,8-pregnatriene-3,20-dione.

(b) One gram of the crude 17α-acetoxy-11β,21-dihydroxy-1,4,8-pregnatriene-3,20-dione in 6 ml. of pyridine is stirred with 3 ml. of acetic anhydride for 1 hour at room temperature. The usual working-up step is used to isolate 0.9 g. of a crude product which is purifed on 100 g. of silica gel with a methylene chloride-acetone gradient (0–12% acetone). Yield: 420 mg. of 17α,21-diacetoxy-11β-hydroxy-1,4,8-pregnatriene-3,20-dione, m.p. 220°.

EXAMPLE 16

2.5 g. of crude 17α-acetoxy-11β,21-dihydroxy-1,4,8-pregnatriene-3,20-dione is agitated overnight at room temperature in 25 ml. of pyridine and 12 ml. of n-valeric anhydride. The mixture is worked up as usual, and the crude product is purified on 500 g. of silica gel with a methylene cloride-acetone gradient (0–12% acetone). Yield: 1.1 g. of 17α-acetoxy-11β-hydroxy-21-valeryloxy-1,4,8-pregnatriene-3,20-dione.

EXAMPLE 17

Analogously to Example 16, 2.1 g. of crude 17α-acetoxy-11β,21-dihydroxy-1,4,8-pregnatriene-3,20-dione in 25 ml. of pyridine is reacted with 12 ml. of trimethylacetic anhydride. The crude product is purified on 400 g. of silica gel with a methylene chloride-acetone gradient (0–12% acetone), thus isolating 850 mg. of 17α-acetoxy-11β-hydroxy-21-trimethylacetoxy-1,4,8-pregnatriene-3,20-dione.

EXAMPLE 18

20 g. of 11β,17α,21-trihydroxy-1,4,8-pregnatriene-3,20-dione is reacted analogously to Example 15 with the triethyl ester of orthopropionic acid and then hydrolyzed. The thus-obtained 5 g. of crude product is purified on 600 g. of silica gel with a hexane-ethyl acetate gradient (0–100% ethyl acetate). Yield: 2.1 g. of 11β,21-dihydroxy-17α-propionyloxy-1,4,8-pregnatriene-3,20-dione, m.p. 216°.

EXAMPLE 19

1.2 g. of purified 11β,21-dihydroxy-17α-propionyloxy-1,4,8-pregnatriene-3,20-dione is stirred with 10 ml. of formic acid for 24 hours at room temperature. After precipitation into ice water, the mixture is filtered off, the residue is dissolved in methylene chloride, and the solution is washed with sodium bicarbonate and water untl neutral. After drying, the mixture is concentrated, thus isolating 45 mg. of 21-formyloxy-11β-hydroxy-17α-propionyloxy-1,4,8-pregnatriene-3,20-dione.

EXAMPLE 20

700 mg. of crude 11β,21-dihydoxy-17α-propionyloxy-1,4,8-pregnatriene-3,20-dione is reacted analogously to Example 15 with acetic anhydride, thus isolating 700 mg. of a crude product which is purified on 800 g. of silica gel with a methylene chloride-acetone gradient (0–12% acetone). Yield: 385 mg. of 21-acetoxy-11β-hydroxy-17α-propionyloxy-1,4,8-pregnatriene-3,20-dione, m.p. 213°.

EXAMPLE 21

1.5 g. of crude 11β,21-dihydroxy-17α-propionyloxy-1,4,8-pregnatriene-3,20-dione in 9 ml. of pyridine is reacted with 5 ml. of propionic anhydride for 1 hour at room temperature. The mixture is worked up as usual. A crude yield of 1.4 g. of obtained which is chromatographed on 160 g. of silica gel with a methylene chloride-acetone gradient (0–12% acetone), thus isolating 620 mg. of 11β-hydroxy-17α,21-dipropiionyloxy-1,4,8-pregnatriene-3,20-dione, m.p. 191°.

EXAMPLE 22

1.1 g. of crude 11β,21-dihydroxy-17α-propionyloxy-1,4,8-pregnatriene-3,20-dione in 12 ml. of pyridine is stirred with 6 ml. of butyric anhydride overnight at room temperature. The crude product obtained after working the reaction mixture up as usual is purified on 120 g. of silica gel with a methylene chloride-acetone gradient (0–12% acetone). Yield: 510 mg. of 21-butyryloxy-11β-hydroxy-17α-propionyloxy-1,4,8-pregnatriene-3,20dione, m.p. 163°.

EXAMPLE 23

Analogously to Example 16, 1.3 g. of 11β,21-dihydroxy-17α-propionyloxy-1,4,8-pregnatriene-3,20-dione in 15 ml. of pyridine is reacted with 8 ml. of n-valeric anhydide. The crude yield of 2.5 g. of purified on 200 g. of silica gel with a methylene chloride-acetone gradient (0–12% acetone), thus isolating 535 mg. of 11β-propionyloxy-21-valeryloxy-1,4,8-pregnatriene-3,20-dione, m.p. 147°.

EXAMPLE 24

1.6 g. of 11β,21-dihydroxy-17α-propionyloxy-1,4,8-pregnatriene-3,20-dione in 30 ml. of pyridine is stirred at room temperature with 15 ml. of caproic anhydride for 1.5 hours. The mixture is then precipitated into ice water and worked up as usual, thus isolating 3.1 g. of a crude product. Chromatography on 300 g. of silica gel with a methylene chloride-acetone gradient (0–12% acetone) yields 1.23 g. of 21-hexanoyloxy-11β-hydroxy-17α-propionyloxy-1,4,8-pregnatriene-3,20-dione, m.p. 162°.

EXAMPLE 25

1.5 g. of crude 11β,21-dihydroxy-17α-propionyloxy-1,4,8-pregnatriene-3,20-dione in 15 ml. of pyridine and 10 ml. of enanthic anhydride is agitated overnight at room temperature. The mixture is worked up as usual, and the excess enanthic acid is removed by steam distillation. The crude product is chromatographed on 300 g. of silica gel with a methylene chloride-acetone gradient (0–12% acetone), thus isolating 680 mg. of 21-heptanoyloxy-11β-hydroxy-17α-propionyloxy-1,4,8-pregnatriene-3,20-dione.

EXAMPLE 26

1.9 g. of crude 11β,21-dihydroxy-17α-propionyloxy-1,4,81-pregnatriene-3,20-dione is reacted analogously to Example 17 with trimethylacetic anhydride. The crude product is chromatographed on 400 g. of silica gel with a methylene chloride-acetone gradient (0–12% acetone). Yield: 620 mg. of 11β-hydroxy-17α-propionyloxy-21-trimethylacetoxy-1,4,8-pregnatriene-3,20-dione.

EXAMPLE 27

1.4 g. of crude 17α-butyryloxy-11β,21-dihydroxy-1,4,8-pregnatriene-3,20-dione is reacted analogously to Example 15 with acetic anhydride. The crude product is chromatographed on 250 g. of silica gel with a methylene chloride-acetone gradient (0–12% acetone), thus obtaining 785 mg. of 21-acetoxy-17α-butyryloxy-11β-hydroxy-1,4,8-pregnatriene-3,20-dione.

EXAMPLE 28

Analogously to Example 26, 1.2 g. of 17α-butyryloxy-11β,21-dihydroxy-1,4,8-pregnatriene-3,20-dione is reacted with trimethylacetic anhydride. The product is purified on 200 g. of silica gel with a methylene chloride-acetone gradient (0–12% acetone). Yield: 345 mg. of 17α-butyryloxy-11β-hydroxy-21-trimethylacetoxy-1,4,8-pregnatriene-3,20-dione.

EXAMPLE 29

Analogously to Example 24, 900 mg. of 17α-butyryloxy-11β,21-dihydroxy-1,4,8pregnatriene-3,20-dione is reacted wih caproic anhydride. The crude product is chromatographed on 150 g. of silica gel with a methylene chloride-acetone gradient (0–12% acetone), thus isolating 410 mg. of 17α-butyryloxy-21-hexanoyloxy-11β-hydroxy-1,4,8-pregnatriene-3,20-dione.

EXAMPLE 30

Analogously to Example 21, 1.1 g. of crude 11β,21-dihydroxy-17α-valeryloxy-1,4,8-pregnatriene-3,20-dione is reacted with propionic anhydride, and the crude product is purified on 160 g. of silica gel with a methylene chloride-acetone gradient (0–12% acetone). Yield: 562 mg. of 11β-hydroxy-21-propionyloxy-17αvaleryloxy-1,4,8-pregnatriene-3,20-dione.

EXAMPLE 31

Analogously to Example 23, one gram of crude 11β,21-dihydroxy-17α-valeryloxy-1,4,8-pregnatriene-3,20-dione is reacted with n-valeric anhydride. The dried product is purified on 160 g. of silica gel with a methylene chloroform-acetone gradient (0–12% acetone), thus obtaining 490 mg. of 11β-hydroxy-17α,21-divaleryloxy-1,4,8-pregnatriene-3,20-dione.

EXAMPLE 32

4 g. of 17α-benzoyloxy-9α-chloro-11β,21-dihydroxy-1,4-pregnadiene-3,20-dione in 80 ml. of hexamethylphosphoric triamide is agitated with 4 g. of lithium chloride for 3.5 hours at 80°. After precipitation into ice water and working up the product as usual, 3.2 g. of a crude compound is obtained of which 2.2 g. is chromatographed on 250 g. of silica gel with a methylene chloride-acetone gradient (0–20% acetone). Yield: 630 mg. of 17α-benzoyloxy-11β,21-dihydroxy-1,4,8-pregnatriene-3,20-dione, m.p. 198° (decomposition).

EXAMPLE 33

One gram of crude 17α-benzoyloxy-11β,21-dihydroxy-1,4,8-pregnatriene-3,20-dione is acetylated analogously to Example 15, aand the crude product is purified on 120 g. of silica gel with a methylene chloride-acetone gradient (0–12% acetone). Yield: 672 mg. of 21-acetoxy-17α-benzoyloxy-11β-hydroxy-1,4,8-pregnatriene-3,20-dione, m.p. 215° (decomposition).

EXAMPLE 34

Analogously to Example 17, 1.2 g. of crude 17α-benzoyloxy-11β,21-dihydroxy-1,4,8-pregnatriene-3,20-dione is reacted wth trimtheylacetic anhydride. The crude product is purified on 160 g. of silica gel with a methylene chloride-acetone gradient (0–12% acetone). Yield: 743 mg. of 17α-benzoyloxy-11β-hydroxy-21trimethylacetoxy-1,4,8-pregnatriene-3,20-dione, m.p. 135°.

EXAMPLE 35

1.3 g. of crude 17α-benzoyloxy-11β,21-dihydroxy-1,4,8-pregnatriene-3,20-dione is reacted with carproic anhydride analogously to Example 24. The crude product is chromatographed on 120 g. of silica gel with a methylene chloride-acetone gradient (0–12% acetone), thus isolating 790 mg. of 17α-benzoyloxy-21-hexanoyloxy-11β-hydroxy-1,4,8-pregnatriene-3,20-dione.

EXAMPLE 36

Under the conditions of Example 8, 700 mg. of 17α-acetoxy-11β-hydroxy-21-trimethylacetoxy-1,4,8-pregnatriene-3,20-dione is oxidized. The crude product is chromatographed on 120 g. of silica gel with a methylene cloride-acetone gradient -(0–12% acetone), thus obtaining 384 mg. of 17α-acetoxy-21-trimethylacetoxy-1,4,8-pregnatriene-3,11,20-trione.

EXAMPLE 37

Analogously to Example 8, 850 mg. of 11β-hydroxy-17α,21-dipropionyloxy-1,4,8-pregnatriene-3,20-dione is oxidized with chromium trioxide. The crude product is purified on 120 g. of silica gel with a methylene chloride-acetone gradient (0–12% acetone). Yield: 565 mg. of 17α,21-dipropionyloxy-1,4,8-pregnatriene-3,11,20-trione.

EXAMPLE 38

900 mg. of 17α-butyryloxy-21-hexanoyloxy-11β-hydroxy-1,4,8-pregnatriene-3,20-dione is oxidized analogously to Example 8. The crude product is chromatographed on 120 g. of silica gel with a methylenechloride-acetone gradient (0–12% acetone), thus isolating 715 mg. of 17α-butyryloxy-1,4,8-pregnatriene-3,11,20-trione.

EXAMPLE 39

One gram of 21-acetoxy-17α-benzoyloxy-11β-hydroxy-1,4,8-pregnatriene-3,20-dione is oxidized analogously to Example 8. After purification on 120 g. of silica gel with a methylene chloride-acetone gradient (0–12% acetone), 840 mg. of 21-acetoxy-17α-benzoyloxy-1,4,8-pregnatriene-3,11,20-trione isolated which is recrystallized from acetone-hexane. Melting point: 249° (decomposition).

EXAMPLE 40

[(a) Analogously to Example 15, 5 g. of 17α-benzoyloxy-9α-chloro-11β-fluoro-21-hydroxy-1,4-pregnadiene-3,20-dione is reacted with acetic anhydride. The crude product is purified on 500 g. of silica gel with a hexane-ethyl acetate gradient (0–40% ethyl acetate), thus isolating 4.9 g. of 21-acetoxy-17α-benzoyloxy-9α-chloro-11β-fluoro-1,4-pregnadiene-3,20-dione.

(b) 700 mg. of the above acetate is stirred in 14 ml. of hexamethylphosphoric triamide with 700 mg. of lithium chloride for 17 hours at a bath temperature of 40°-50°. After precipitation into ice water and working up the reaction mixture as usual, 750 mg. of a crude product is isolated which is purified on 120 g. of silica gel with a hexane-ethyl acetate gradient (0–40% ethyl acetate). Yield: 370 mg. of 21-acetoxy-17α-benzoyloxy-11β-fluoro-1,4,8-pregnatriene-3,20-dione, m.p. 236° (decomposition).

EXAMPLE 41

(a) Analogously Example 17, 2 g. of 17α-benzoyloxy-9α-chloro-11β-fluoro-1,4-pregnadiene-3,20-dione is reacted with trimethylacetic anhyride. The crude product is purified on 250 g. of silica gel with a hexane-ethyl acetate gradient (0–40% ethyl acetate), thus isolating 1.72 g. of 17α-benzoyloxy-9α-chloro-11β-fluoro-21-trimethylacetoxy-1,4-pregnadiene-3,20-dione.

(b) 1.5 g. of the trimethyl acetate is treated analogously to Example 40 with lithium chloride, and the crude product is purified on 160 g. of silica gel with a hexane-ethyl acetate gradient (0–40% ethyl acetate). Yield: 780 mg. of 17α-benzoyloxy-11β-fluoro-21-trimethylacetoxy-1,4,8-pregnatriene-3,20-dione.

EXAMPLE 42

(a) 10 g. of 17α-benzoyloxy-9α-chloro-11β,21-dihydroxy-1,4-pregnadiene-3,20-dione in 150 ml. of pyridine is agitated with 14.2 g. of β-benzoylpropionic acid and 6.85 g. of dicyclohexylcarbodiimide for 144 hours at room temperature. After the reaction mixture has been worked up as usual, the crude product is purified on 2.3 kg. of silica gel with a methylene chloride-acetone gradient (0–20% acetone). Yield: 3.7 g. of 17α-benzoyloxy-21-(2-benzoylpropionyloxy)-9α-chloro-11β-hydroxy-1,4-pregnadiene-3,20-dione, m.p. 199°.

(b) 3.7 g. of the above-mentioned compound in 74 ml. of hexamethylphosphoric triamide is stirred at 80° for 6.5 hours with 3.7 g. of lithium chloride. After the reaction mixture has been worked up as usual, 3.2 g. of a crude product is isolated which is chromatographed on 200 g. of silica gel with a methylene chloride-acetone gradient (0–12% acetone). Yield: 831 mg. of 17α-benzoyloxy-21-(2-benzoylpropionyloxy)-11β-hydroxy-1,4,8-pregnatriene-3,20-dione, m.p. 203.5°.

The preceding examples can be repeated with similar success by substituting the generically and specifically described reactants and/or operating conditions of this invention for those used in the preceeding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Corticoids of the formula

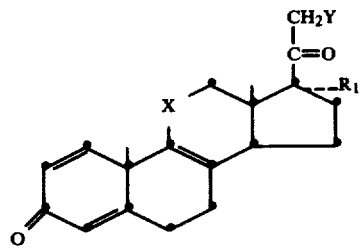

wherein
X is β-hydroxymethylene, β-fluoromethylene or carbonyl;
Y is fluorine or chlorine; and
$R_1$ is acyloxy of 1–10 carbon atoms.

2. 17α-Acetoxy-21-chloro-11β-hydroxy-1,4,8-pregnatriene-3,20-dione, a compound of claim 1.

3. 21-Chloro-11β-hydroxy-17α-propionyloxy-1,4,8-pregnatriene-3,20-dione, a compound of claim 1.

4. 17α-Butyryloxy-21-chloro-11β-hydroxy-1,4,8-pregnatriene-3,20-dione, a compound of claim 1.

5. 21-Chloro-11β-hydroxy-17α-valeryloxy-1,4,8-pregnatriene-3,20-dione, a compound of claim 1.

6. 21-Chloro-17α-hexanoyloxy-11β-hydroxy-1,4,8-pregnatriene-3,20-dione, a compound of claim 1.

7. 21-Chloro-17α-cyclohexylcarbonyloxy-11β-hydroxy-1,4,8-pregnatriene-3,20-dione, a compound of claim 1.

8. 17α-Benzoyloxy-21-chloro-11β-hydroxy-1,4,8-pregnatriene-3,20-dione, a compound of claim 1.

9. 17α-Benzoyloxy-21-chloro-1,4,8-pregnatriene-3,11,20-trione, a compound of claim 1.

10. 21-Chloro-17α-propionyloxy-1,4,8-pregnatriene-3,11,20-trione, a compound of claim 1.

11. 17α-Butyryloxy-21-chloro-1,4,8-pregnatriene-3,11,20-trione, a compound of claim 1.

12. 17α-Benzoyloxy-21-fluoro-11β-hydroxy-1,4,8-pregnatriene-3,20dione, a compound of claim 1.

13. 21-Fluoro-11β-hydroxy-17α-propionyloxy-1,4,8-pregnatriene-3,20dione, a compound of claim 1.

14. 21-Fluoro-17α-propionyloxy-1,4,8-pregnatriene-3,11,20trione, a compound of claim 1.

15. 17α-Benzoyloxy-21-chloro-11β-fluoro-1,4,8-pregnatriene-3,20dione, a compound of claim 1.

* * * * *